US006048688A

United States Patent [19]
Korth et al.

[11] Patent Number: 6,048,688
[45] Date of Patent: Apr. 11, 2000

[54] **METHOD FOR DETECTION OF *PSEUDOMONAS AERUGINOSA* USING POLYMERASE CHAIN REACTION**

[75] Inventors: Kevin Gary Korth, Appleton; Sarah Elizabeth Heathcock, Menasha; Linda Susan Huard, Appleton, all of Wis.

[73] Assignee: Kimberly-Clark Corporation, Neenah, Wis.

[21] Appl. No.: 08/748,170

[22] Filed: Nov. 12, 1996

[51] Int. Cl.[7] .............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search .................................. 536/22.1, 24.3, 536/25.3; 435/91.1, 91.2, 6

[56] References Cited

U.S. PATENT DOCUMENTS

| | | | |
|---|---|---|---|
| 4,458,066 | 7/1984 | Caruthers et al. | 536/27 |
| 4,683,195 | 7/1987 | Mullis et al. | 435/6 |
| 4,683,202 | 7/1987 | Mullis | 435/91 |
| 4,711,955 | 12/1987 | Ward et al. | 536/29 |
| 4,755,458 | 7/1988 | Rabbani et al. | 435/5 |
| 4,780,405 | 10/1988 | Kaiser et al. | 435/6 |
| 4,833,251 | 5/1989 | Musso et al. | 548/303 |
| 4,910,300 | 3/1990 | Urdea et al. | 536/287 |
| 4,965,188 | 10/1990 | Mullis et al. | 435/6 |
| 5,035,996 | 7/1991 | Hartley | 435/6 |
| 5,084,565 | 1/1992 | Parodos et al. | 536/27 |
| 5,130,238 | 7/1992 | Malek et al. | 435/91 |
| 5,130,446 | 7/1992 | Musso et al. | 549/223 |
| 5,175,269 | 12/1992 | Stavrianopoulos | 536/27 |
| 5,217,862 | 6/1993 | Barns et al. | 435/6 |
| 5,241,060 | 8/1993 | Engelhardt et al. | 536/27 |
| 5,328,824 | 7/1994 | Ward et al. | 435/6 |
| 5,348,855 | 9/1994 | Dattagupta et al. | 435/6 |
| 5,376,528 | 12/1994 | King et al. | 435/6 |
| 5,409,818 | 4/1995 | Davey et al. | 435/91.21 |
| 5,447,841 | 9/1995 | Gray et al. | 435/6 |
| 5,447,848 | 9/1995 | Barns et al. | 435/29 |
| 5,491,224 | 2/1996 | Bittner et al. | 435/6 |
| 5,599,665 | 2/1997 | Barbieri et al. | 435/6 |

FOREIGN PATENT DOCUMENTS

| | | |
|---|---|---|
| 0 070 687 | 1/1983 | European Pat. Off. . |
| WO86/06726 | 11/1986 | WIPO . |
| WO 88/03957 A1 | 6/1988 | WIPO .............................. C12Q 1/68 |

OTHER PUBLICATIONS

Khan, A.A. and C.E. Cerniglia, "Detection of *Pseudomonas Aeruginosa* from Clinical and Environmental Samples by Amplification of the Exotoxin A Gene Using PCR," *Applied and Environmental Microbiology*, Oct. 1994, pp. 3739–3745.

Viscidi, R. P., et al., "Novel Chemical Method for the Preparation of Nucleic Acids for Nonisotopic Hybridization," *Journal of Clinical Microbiology*, vol. 23, No. 2 (Feb. 1986), pp. 311–317.

Avignolo, C., et al., "Biotinylation of Double Stranded DNA After Transamination," *Biochemical and Biophysical Research Communications*, vol. 170, No. 1 (Jul. 1990), pp. 243–250.

Hayatsu, H., "Reaction of Cytidine with Semicarbazide in the Presence of Bisulfite. A Rapid Modification Specific for Single–Stranded Polynucleotide," *Biochemistry*, vol. 15, No. 12 (1976), pp. 2677–2682.

Draper, D. B., et al., "A Method for Linking Fluorescent Labels to Polynucleotides: Application to Studies of Ribosome–Ribonucleic Acid Interactions," *Biochemistry*, vol. 19, No. 9 (1980), pp. 1774–1781.

Schulman, L. H., et al., "Attachment of protein affinity–labeling reagents of variable length and amino acid specificity to *E. coli* tRNA$^{fMet}$," *Nucleic Acids Research*, vol. 9, No. 5 (1981), pp. 1203–1217.

Eshaghpour, H., et al., "Specific chemical labeling of DNA fragments," *Nucleic Acids Research*, vol. 7 No. 6 (Aug. 1979), pp. 1485–1495.

Yang, C., et al., "Covalent Attachment of Fluorescent Groups to Transfer Ribonucleic Acid Reactions with 4–Bromomethyl–7–methoxy–2–oxo–2H–benzopyran," *Biochemistry*, vol. 13, No. 17(1974), pp. 3615–3621.

Reines, S. A., et al., "A New Method for Attachment of Fluorescent Probes to tRNA," *Methods in Enzymology*, vol. LIX, [7], pp. 146–156.

Landegent, J.E., et al., "2–Acetylaminofluorene–modified Probes for the Indirect Hyrbridocytochemical Detection of Specific Nucleic Acid Sequences," *Experimental Cell Research*, vol. 153 (1984), pp. 61–72.

Hopman, A. H. N., et al., "Bi–color detection of two target DNAs by non–radioative in situ hybridization," *Histochemistry*, vol. 85,(1986), pp. 1–4.

Nociari et al, Diagnostic Microbiology and Infectious Disease 24 :179–190 (1996).

Gray et al. Cloning, nucleotide sequence, and expression in *Escherichia coli* of the exotoxin A structural gene of *Pseudomonas aeruginosa* Proc. Natl. Acad. Sci. USA, vol. 81, pp. 2645–2649, 1984.

*Primary Examiner*—W. Gary Jones
*Assistant Examiner*—Ethan Whisenant
*Attorney, Agent, or Firm*—Jones & Askew, LLP

[57] ABSTRACT

The present invention relates to a method for detecting the presence of *P. aeruginosa* in a fluid sample. The method uses PCR to amplify the expression of a segment of the exotoxin A gene sequence. The method includes treating strands of nucleotide fragments with a first oligonucleotide primer and a second oligonucleotide primer. The primers are sufficiently complementary to the fragment to hybridize a region having from about 400 to 1200 base pairs. Desirably, the first oligonucleotide primer includes the sequence 5'-ACA ACG CCC TCA GCA TCA CCA-3' and the second oligonucleotide primer includes the sequence 5'-CGG GTC GAG CAG GCA CAA C-3'.

5 Claims, No Drawings

METHOD FOR DETECTION OF *PSEUDOMONAS AERUGINOSA* USING POLYMERASE CHAIN REACTION

BACKGROUND OF THE INVENTION

The present invention relates to an improved method for detecting the presence of *Pseudomonas aeruginosa* (*P. aeruginosa*) in a fluid sample. More specifically, it relates to a method of using specific primers in a polymerase chain reaction (PCR) process to clone a segment of the *P. aeruginosa* exotoxin A (ETA) gene having at least 400 base pairs.

*P. aeruginosa* is an opportunistic pathogen capable of producing two different ADP-ribosyltransferase toxins: ETA and exoenzyme S. Exoenzyme S can cause significant tissue damage in lung, burn and wound infections in both humans and animals. Exotoxin A is highly toxic and is produced by a majority of *P. aeruginosa* strains. The toxin is known to inhibit eucaryotic protein biosynthesis at the level of peptide chain elongation, which is similar to diphtheria toxin. It has been observed that as few as 10 to 100 cells of *P. aeruginosa* can lead to intestinal colonization in patients who are immunosuppressed. A few illustrative causes of immunosuppression include transplant patients, AIDS patients, chemotherapy recipients, and the like.

Since *P. aeruginosa* is medically important, various methods have been developed to identify *P. aeruginosa* species. Such methods include, but are not limited to, using monoclonal antibodies, immunofluorescent antibodies, conventional microbiological methods and DNA or RNA sequencing replication. Each of these methods has, to a limited extent, a disadvantage. The immunofluorescent-antibody test is unreliable because it produces a dull olive green or yellow color which is hard to distinguish from autofluorescense. Conventional microbiological methods, although accurate, are very time intensive since active organisms must be cultured and isolated. This usually requires several days under ideal conditions. Using DNA or RNA sequencing techniques require a measurable amount of DNA or RNA to work. Plus, the probe chosen must be specific enough so as to exclude other organisms that may have a similar nucleic acid sequence. To overcome these disadvantages, DNA/RNA primers and probes have had to have a substantial number of nucleotides to be specific to a targeted gene fragment within the organism.

To overcome the disadvantages associated with the low amount of DNA/RNA present in a test sample PCR can be used, under hybridizing conditions, to multiply the targeted gene core fragment. PCR synthetically increases the nucleotide material present without necessarily having a large number of organisms initially to derive starting genetic material.

Briefly, PCR involves treating a DNA sample, under hybridizing conditions, with one oligonucleotide primer for each strand of each different specific sequence suspected of being present in the sample. Using the primers and agents for polymerization, an extension product of each primer is synthesized which is complementary to each nucleic acid strand. The primer or primers are selected to be substantially complementary to each targeted strand of each specific sequence such that the extension product synthesized from one primer, when it is separated from its complement, can serve as a template for synthesis of the extension product. The hybridized core fragment is then denatured, generally using heat, to separate the primer extension products. These products are again subjected to complementary nucleotide primers such that a primer extension product is synthesized using each of the single strands produced as a template, resulting in amplification of the specific nucleic acid sequence or sequences if present. This process is cycled sufficiently to increase the amount of targeted DNA so that detection is possible.

A disadvantage of using PCR is that the oligonucleotide primers must be sufficiently long to specifically hybridize a targeted segment of the nucleotide fragment which itself must be unique to the targeted organism. If the oligonucleotide primers are too long, there is a possibility that the primers will autopolymerize reducing the efficacy of the selected primers. If the oligonucleotide primers are not long enough then they may not be specific to the targeted fragment or organism leading to no differentiation between a targeted organism and a non-targeted organism. Accordingly, there is a need for a primer for detecting *P. aeruginosa* which will reduce or eliminate autopolymerization and have a high sensitivity for the target organism, *P. aeruginosa*.

SUMMARY OF THE INVENTION

Briefly the invention relates to a method for detecting *Pseudomonas aeruginosa* in a fluid sample. The method includes using PCR techniques to increase the expression of a segment of an exotoxin A (ETA) gene sequence (SEQ ID NO: 3 fragment. The method includes treating single strands of nucleotide fragments with a first and a second oligonucleotide primer. The primers are sufficiently complementary to the nucleotide fragment so that the PCR process will hybridize a region of the fragment having from about 400 base pairs to about 1200 base pairs. In a preferred embodiment the first oligonucleotide primer includes the sequence 5'-ACA ACG CCC TCA GCA TCA CCA-3' (SEQ ID NO: 4) and hybridizes the region of 1002 to about 1023 of the ETA gene sequence (SEQ ID NO: 3). The second oligonucleotide primer includes the sequence 5'-CGG GTC GAG CAG GCA CAA C-3' (SEQ ID NO: 5) and hybridizes the region of 1405 to about 1424 region of the ETA gene sequence.

It is a general object of the invention to provide a method for detecting the presence of *P. aeruginosa* in a fluid sample. A more specific object of the invention is to provide a method for detecting *P. aeruginosa* using PCR techniques in conjunction with specific oligonucleotide primers to hybridize a region of the ETA gene sequence (SEQ ID NO: 3) having from about 400 to about 1200 base pairs.

It is another object of the invention to provide a method which is highly sensitive in detecting the presence of *P. aeruginosa* in a fluid sample using specific primers.

DETAILED DESCRIPTION OF THE INVENTION

The term "oligonucleotide" as used herein when referring to primers, probes, oligomer fragments to be detected, and the like is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. It will be understood that the word primer as used herein may refer to more than one primer. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand.

Hybridization traditionally is understood as the process by which, under predetermined reaction conditions, two partially or completely complementary single-stranded nucleic acids are allowed to come together in an anti-parallel fashion to form a double-stranded nucleic acid with specific and stable hydrogen bonds.

The present invention is directed to a method of detecting *P. aeruginosa* in a fluid sample. The method uses PCR to amplify at least one specific nucleic acid sequence in the organism's exotoxin A gene. The method includes treating strands of nucleotide fragments with a first and second oligonucleotide primer. The region of the gene being amplified by the PCR process has a left segment at the 5' end of the gene, a core segment and a right segment at the 3' end of the gene. The left segment and right segments of the ETA gene are substantially complementary to the first oligonucleotide primer and second oligonucleotide primers, respectively. The core segment is composed of nucleotides between the first and second primers corresponding to the 5' and 3' ends of the ETA gene.

The nucleic acid or acid constituting the core nucleotides may be obtained from any source, for example, cloned DNA or RNA, or natural DNA or RNA from bacteria, yeast, viruses, or other organisms such as plants or animals. The PCR process is described in greater detail in U.S. Pat. Nos. 4,683,202; 4,683,195; and 4,965,188 the entire contents of each being incorporated herein and made a part hereof.

The oligonucleotide primers are sufficiently complementary to the ETA gene nucleotide fragment to hybridize a region having from about 400 to about 1200 base pair nucleotides. Desirably, the oligonucleotide primers are sufficiently complementary to hybridize from about 400 to about 800 base pair nucleotides and more desirably, the oligonucleotide primers hybridize from about 400 to about 600 base pair nucleotides. The oligonucleotide primers can have from about 15 nucleotides to about 25 nucleotides each. The oligonucleotide primers may be prepared using methods well known in the art. For example, one method for synthesizing oligonucleotides on a modified solid support is described in U.S. Pat. No. 4,458,066, the entire contents being incorporated herein and made a part hereof. It is also possible to use a primer which has been isolated from a biological source (such as a restriction endonuclease digest).

In a preferred embodiment the first and second oligonucleotide primers are complementary to and hybridizes to the fragment within the ETA gene sequence (SEQ ID NO: 3) region of 1002 to about 2200. Preferably, the first and second oligonucleotide primers are complementary to and hybridizes to the fragment within the ETA gene sequence (SEQ ID NO: 3) region of 1002 to about 1500 and more preferably, are complementary to and hybridizes to the fragment within the ETA gene sequence (SEQ ID NO: 3) region of 1002 to about 1424. Most preferably the first oligonucleotide primer includes the nucleotide sequence 5'-ACA ACG CCC TCA GCA TCA CCA-3' (SEQ ID NO: 4) and the second oligonucleotide primer includes the nucleotide sequence 5'-CGG GTC GAG CAG GCA CAA C-3' (SEQ ID NO: 5) which are complementary to and targeted at the ETA gene sequence (SEQ ID NO: 3) regions of 1002 to 1023 and 1405 to 1424, respectively.

The following examples are offered by way of illustration and are not intended to limit the invention in any manner. In these examples, all percentages are by weight if for solids and by volume if for liquids. All temperatures are in degrees Celsius unless otherwise noted.

COMPARATIVE EXAMPLES

A polymerase chain reaction was performed to amplify a region of the exotoxin A gene of *P. aeruginosa*. The sequence of the left (5') and right (3') primers were SEQ. ID NO: 1 and SEQ ID NO: 2 respectively. These primers are known in the prior art to target the ETA gene sequence (SEQ ID NO: 3) fragment at positions 1001–1024 and 1373–1396 respectively.

Purified DNA, used as template, was isolated from *P. aeruginosa* ATCC 15442 grown overnight in Luria-Bertaini broth at 37° C. using the QIAGEN (Chatsworth, Calif.) Genomic Isolation Kit with 20/G columns. Purified DNA was resuspended in TE8 (10 mM Tris-HCl, 1 mM EDTA, pH 8). Concentration was determined spectrophotometrically at a wavelength of 260 nm.

The PCR reaction mix was set up 50 μl per reaction per tube, eight tubes (0.2 ml dome-capped PCR reaction tubes). The reaction mix for each tube consisted of: 35.75 μl of sterile $ddH_2O$, 5 μl 10× reaction buffer (standard Perkin-Elmer 10× buffer: 100 mM Tris-HCl [pH 8.3], 500 mM KCl, 15 mM $MgCl_2$, 0.1% gelatin), 5 μl deoxynucleotide triphosphates (2.0 mM each dATP, dTTP, dGTP, and dCTP) 1 μl of each primer (stock concentration 50 μM), and 0.25 μl (0.5 U/μl) AmpliTaq® polymerase (Perkin-Elmer). Starting with 200,000 pg, 2 μl of 10-fold serial dilutions the purified genomic DNA was added to each tube (200,000 pg to tube 1, 20,000 pg to tube 2, etc.). Tube 8 contained no DNA, rather, 2 μl of sterile TE8 was added as the "no template control late control." The samples were capped tightly and placed in the thermocycler (Perkin-Elmer model 2400) without oil overlay (not required for model 2400). One pre-PCR cycle was run (94° C. for three minutes followed by 68° C. for two minutes). Forty regular PCR cycles were run (72° C. for one minute, 94° C. for one minute, and 68° C. for one minute), followed by one final 72° C. for eight minutes and then held at 4° C. until loaded on the gel (2% low-melting agarose, 10×17 cm, containing 0.5 μg/ml ethidium bromide) was loaded by adding 25 μl from each tube of the PCR reaction to 5 μl of 6× loading buffer (0.25% bromphenol blue, 0.25% xylene cyanol FF, 30% glycerol in waster) and the entire 30 μl was loaded into a well (lane) of the gel. Lane 1 of the gel contained a 2× load of 100-bp ladder DNA (Boehringer Mannheim DNA molecular weight standard XI). The gel was run for 10 minutes at 30 volts and 90 minutes at 125 volts. The gel was then photographed under UV, using Polaroid 660 instant black-and-white film. The photograph was evaluated visually for the presence of the desired band.

The results are tabulated in Table 1 below.

TABLE 1

| Tube Number | Amount of template DNA in tube | Amplification seen visually on gel |
|---|---|---|
| 1 | 200,000 pg | + |
| 2 | 20,000 pg | − |
| 3 | 2,000 pg | − |
| 4 | 200 pg | − |
| 5 | 20 pg | − |
| 6 | 2 pg | − |
| 7 | 0.2 pg | − |
| 8 | no template control | − |

EXAMPLES

Purified DNA from isolated *P. aeruginosa* ATCC 15442 as discussed above was used in the examples below.

In accordance with the present invention, a polymerase chain reaction was performed according to the following procedures. The left (5') and right (3') primers were SEQ. ID NO: 4 and SEQ. ID NO: 5 respectively. These primers amplify a 422 base pair region of the ETA gene sequence (SEQ ID NO: 3) at the positions 1002–1023 and 1405–1424 respectively.

The PCR reaction mix was set up as a "hot-start" PCR reaction. Hot start PCR reactions keep components of the reaction mix separated by a wax layer until the initial denaturation (94° C.) in the thermocycler. Therefore, each PCR reaction tube, prior to going into the thermocycler, contains an "upper reaction mix" and a "lower reaction mix" separated by the wax layer. The overall reaction was set up for a 50 µl total volume per tube (0.2 ml dome-cap PCR reaction tube), eight total tubes. The lower reaction mix (below the wax layer) consisted of (per tube): 4.91 µl sterile ddH$_2$O, 1.25 µl 10× PCR Buffer (100 mM Tris-HCl pH 9.2, 35 mM MgCl$_2$, 250 mM KCl), 5 µl deoxynucleotide triphosphate mix (2 mM each of dATP, dCTP, dGTP, dTTP), 0.67 µl ETA3 primer (50 µM stock), and 0.67 µl ETA4 primer (50 µM stock). A wax bead (Perkin Elmer PCR Gem 50) was placed in each tube and all tubes were heated to 80° C. briefly to melt the wax and seal off the lower layer. The upper layer (placed over the lower layer) consisted of (per tube): 29 µl sterile ddH$_2$O, 3.75 µl 10× PCR Buffer (same composition as lower layer), 2.5 µl dimethylsulfoxide, 0.25 µl AmpliTaq® polymerase (Perkin-Elmer), and 2 µl of the serial dilution of purified *P. aeruginosa* genomic DNA. The DNA was added as described above (200,000 pg to tube 1, 20,000 pg to tube 2, etc.) A "no template" control was included (tube 8) which contained only TE8 buffer in place of the DNA. The samples were placed in the thermocycler (Perkin-Elmer model 2400) without oil overlay (not required for model 2400). One pre-PCR cycle was run (94° C. for three minutes followed by 65° C. for two minutes). Forty regular PCR cycles were run (72° C. for 1 minute, 94° C. for one minute, and 65° C. for one minute), followed by one final 72° C. for five minutes and then held at 4° C. until loaded on the gel. The gel (2% low-melting agarose, 10×17 cm, containing 0.5 µg/ml ethidium bromide) was loaded by adding 25 µl from each tube of the PCR reaction to 5 µl of 6× loading buffer (0.25% bromphenol blue, 0.25% xylene cyanol FF, 30% glycerol in water) and the entire 30 µl was loaded into a well (lane) of the gel. Lane 1 of the gel contained a 2× load of 100-bp ladder DNA (Boehringer Mannheim DNA molecular weight standard XI). The gel was run for 10 minutes at 30 volts and 90 minutes at 125 volts. The gel was then photographed under UV, using Polaroid 660 instant black-and-white film. The photograph was evaluated visually for the presence of the desired band.

The results appear in Table 2 below.

TABLE 2

| Tube Number | Amount of template DNA in tube | Amplification seen visually on gel |
|---|---|---|
| 1 | 200,000 pg | + |
| 2 | 20,000 pg | + |
| 3 | 2,000 pg | + |
| 4 | 200 pg | + |
| 5 | 20 pg | + |
| 6 | 2 pg | − |
| 7 | 0.2 pg | − |
| 8 | no template control | − |

Comparing the results in Table 1 with those of Table 2 shows that primers ETA3 and ETA4 are 10,000 times more sensitive in detecting the presence of *P. aeruginosa*. Comparison between the prior art primers and the primers in accordance with the invention was made by examining the amplification products on a 2% agarose gel, containing the DNA Stain ethidium bromide. The gel was examined under UV lighting.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pseudomonas aeruginosa (ix) FEATURE:
            (A) NAME/KEY: misc_feature
            (B) LOCATION: 1..24
            (D) OTHER INFORMATION: /note= "GenBank accession number
                K01397; NCBI sequence ID: 151215; Sequences initiate
                PCR amplification only in P. aeruginosa Exotoxin A gene;
                ETA1:positive strand"

(ix) FEATURE:
            (A) NAME/KEY: primer_bind
            (B) LOCATION: 1..24
            (D) OTHER INFORMATION: /note= "Binds to complementary
                sequences within the P. aeruginosa Exotoxin A gene and
                acts as a primer for PCR-mediated amplification"

(x) PUBLICATION INFORMATION:
            (A) AUTHORS: Khan, Ashraf A.
                Cerniglia, Carl E.
            (B) TITLE: Detection of Pseudomonas aeruginosa from
                Clinical and Environmental Samples by
                Amplification of the Exotoxin A Gene Using PCR
            (C) JOURNAL: Appl. Environ. Microbiol.
            (D) VOLUME: 60
            (E) ISSUE: 10
            (F) PAGES: 3739-3745
            (G) DATE: October-1994

(xi) SEQUENCE DESCRIPTION: SEQ ID NO:1:

GACAACGCCC TCAGCATCAC CAGC                                              24

(2) INFORMATION FOR SEQ ID NO:2:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Pseudomonas aeruginosa (ix) FEATURE:
            (A) NAME/KEY: misc_feature
            (B) LOCATION: 1..24
            (D) OTHER INFORMATION: /note= "GenBank accession number
                K01397; NCBI sequence ID: 151215; Sequences initiate
                PCR amplification only in P. aeruginosa; ETA2: negative
                strand"

(ix) FEATURE:
            (A) NAME/KEY: primer_bind
            (B) LOCATION: 1..24
            (D) OTHER INFORMATION: /note= "Sequence binds to
                complementary sequences within the P. aeruginosa Exotoxin
                A gene and acts as a primer for PCR-mediated
                amplification"

(x) PUBLICATION INFORMATION:
            (A) AUTHORS: Khan, Ashraf A.
                Cerniglia, Carl E.
            (B) TITLE: Detection of Pseudomonas aeruginosa from
                Clinical and Environmental Samples by
                Amplification of the Exotoxin A Gene Using PCR
            (C) JOURNAL: Appl. Environ. Microbiol.
            (D) VOLUME: 60
            (E) ISSUE: 10

(F) PAGES: 3739-3745
                (G) DATE: October-1994

(xi) SEQUENCE DESCRIPTION: SEQ ID NO:2:

CGCTGGCCCA TTCGCTCCAG CGCT                                             24

(2) INFORMATION FOR SEQ ID NO:3:

(i) SEQUENCE CHARACTERISTICS:
                (A) LENGTH: 2760 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Pseudomonas aeruginosa (ix) FEATURE:
                (A) NAME/KEY: misc_feature
                (B) LOCATION: 1..2760
                (D) OTHER INFORMATION: /note= "Found within the published
                    sequence of the P. aeruginosa Exotoxin A gene; GenBank
                    accession number K01397; NCBI sequence ID: 151215 "

(xi) SEQUENCE DESCRIPTION: SEQ ID NO:3:

CTGCAGCTGG TCAGGCCGTT CCGCAACGC TTGAAGTCCT GGCCGATATA CCGGCAGGGC        60

CAGCCATCGT TCGACGAATA AAGCCACCTC AGCCATGATG CCCTTTCCAT CCCCAGCGGA      120

ACCCCGACAT GGACGCCAAA GCCCTGCTCC TCGGCAGCCT CTGCCTGGCC GCCCCATTCG      180

CCGACGCGGC GACGCTCGAC AATGCTCTCT CCGCCTGCCT CGCCGCCCGG CTCGGTGCAC      240

CGCACACGGC GGAGGGCCAG TTGCACCTGC CACTCACCCT TGAGGCCCGG CGCTCCACCG      300

GCGAATGCGG CTGTACCTCG GCGCTGGTGC GATATCGGCT GCTGGCCAGG GGCGCCAGCG      360

CCGACAGCCT CGTGCTTCAA GAGGGCTGCT CGATAGTCGC CAGGACACGC CGCGCACGCT      420

GACCCTGGCG GCGGACGCCG GCTTGGCGAG CGGCCGCGAA CTGGTCGTCA CCCTGGGTTG      480

TCAGGCGCCT GACTGACAGG CCGGGCTGCC ACCACCAGGC CGAGATGGAC GCCCTGCATG      540

TATCCTCCGA TCGGCAAGCC TCCCGTTCGC ACATTCACCA CTCTGCAATC CAGTTCATAA      600

ATCCCATAAA AGCCCTCTTC CGCTCCCCGC CAGCCTCCCC GCATCCCGCA CCCTAGACGC      660

CCCGCCGCTC TCCGCCGGCT CGCCCGACAA GAAAAACCAA CCGCTCGATC AGCCTCATCC      720

TTCACCCATC ACAGGAGCCA TCGCGATGCA CCTGATACCC CATTGGATCC CCCTGGTCGC      780

CAGCCTCGGC CTGCTCGCCG GCGGCTCGTC CGCGTCCGCC GCCGAGGAAG CCTTCGACCT      840

CTGGAACGAA TGCGCCAAAG CCTGCGTGCT CGACCTCAAG GACGGCGTGC GTTCCAGCCG      900

CATGAGCGTC GACCCGGCCA TCGCCGACAC CAACGGCCAG GGCGTGCTGC ACTACTCCAT      960

GGTCCTGGAG GGCGGCAACG ACGCGCTCAA GCTGGCCATC GACAACGCCC TCAGCATCAC     1020

CAGCGACGGC CTGACCATCC GCCTCGAAGG CGGCGTCGAG CCGAACAAGC CGGTGCGCTA     1080

CAGCTACACG CGCCAGGCGC GCGGCAGTTG GTCGCTGAAC TGGCTGGTAC CGATCGGCCA     1140

CGAGAAGCCC TCGAACATCA AGGTGTTCAT CCACGAACTG AACGCCGGCA ACCAGCTCAG     1200

CCACATGTCG CCGATCTACA CCATCGAGAT GGGCGACGAG TTGCTGGCGA AGCTGGCGCG     1260

CGATGCCACC TTCTTCGTCA GGGCGCACGA GAGCAACGAG ATGCAGCCGA CGCTCGCCAT     1320

CAGCCATGCC GGGGTCAGCG TGGTCATGGC CCAGACCCAG CCGCGCCGGG AAAAGCGCTG     1380

```
GAGCGAATGG GCCAGCGGCA AGGTGTTGTG CCTGCTCGAC CCGCTGGACG GGGTCTACAA    1440

CTACCTCGCC CAGCAACGCT GCAACCTCGA CGATACCTGG GAAGGCAAGA TCTACCGGGT    1500

GCTCGCCGGC AACCCGGCGA AGCATGACCT GGACATCAAA CCCACGGTCA TCAGTCATCG    1560

CCTGCACTTT CCCGAGGGCG GCAGCCTGGC CGCGCTGACC GCGCACCAGG CTTGCCACCT    1620

GCCGCTGGAG ACTTTCACCC GTCATCGCCA GCCGCGCGGC TGGGAACAAC TGGAGCAGTG    1680

CGGCTATCCG GTGCAGCGGC TGGTCGCCCT CTACCTGGCG GCGCGGCTGT CGTGGAACCA    1740

GGTCGACCAG GTGATCCGCA ACGCCCTGGC CAGCCCCGGC AGCGGCGGCG ACCTGGGCGA    1800

AGCGATCCGC GAGCAGCCGG AGCAGGCCCG TCTGGCCCTG ACCCTGGCCG CCGCCGAGAG    1860

CGAGCGCTTC GTCCGGCAGG GCACCGGCAA CGACGAGGCC GGCGCGGCCA ACGCCGACGT    1920

GGTGAGCCTG ACCTGCCCGG TCGCCGCCGG TGAATGCGCG GGCCCGGCGG ACAGCGGCGA    1980

CGCCCTGCTG GAGCGCAACT ATCCCACTGG CGCGGAGTTC CTCGGCGACG GCGGCGACGT    2040

CAGCTTCAGC ACCCGCGGCA CGCAGAACTG GACGGTGGAG CGGCTGCTCC AGGCGCACCG    2100

CCAACTGGAG GAGCGCGGCT ATGTGTTCGT CGGCTACCAC GGCACCTTCC TCGAAGCGGC    2160

GCAAAGCATC GTCTTCGGCG GGGTGCGCGC GCGCAGCCAG GACCTCGACG CGATCTGGCG    2220

CGGTTTCTAT ATCGCCGGCG ATCCGGCGCT GGCCTACGGC TACGCCCAGG ACCAGGAACC    2280

CGACGCACGC GGCCGGATCC GCAACGGTGC CCTGCTGCGG GTCTATGTGC CGCGCTCGAG    2340

CCTGCCGGGC TTCTACCGCA CCAGCCTGAC CCTGGCCGCG CCGGAGGCGG CGGGCGAGGT    2400

CGAACGGCTG ATCGGCCATC CGCTGCCGCT GCGCCTGGAC GCCATCACCG GCCCCGAGGA    2460

GGAAGGCGGG CGCCTGGAGA CCATTCTCGG CTGGCCGCTG GCCGAGCGCA CCGTGGTGAT    2520

TCCCTCGGCG ATCCCCACCG ACCCGCGCAA CGTCGGCGGC GACCTCGACC CGTCCAGCAT    2580

CCCCGACAAG GAACAGGCGA TCAGCGCCCT GCCGGACTAC GCCAGCCAGC CCGGCAAACC    2640

GCCGCGCGAG GACCTGAAGT AACTGCCGCG ACCGGCCGGC TCCCTTCGCA GGAGCCGGCC    2700

TTCTCGGGGC CTGGCCATAC ATCAGGTTTT CCTGATGCCA GCCCAATCGA ATATGAATTC    2760
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Pseudomonas aeruginosa (ix) FEATURE:
        (A) NAME/KEY: primer_bind
        (B) LOCATION: 1..21
        (D) OTHER INFORMATION: /note= "DNA primers for initiating
            PCR-mediated amplification of a region of Pseudomonas
            aeruginosa Exotoxin A gene; P. aeruginosa Exotoxin A
            gene-GenBank accession number K01397; NCBI sequence ID: 151215 "

(ix) FEATURE:
(A) NAME/KEY: misc_feature
(B) LOCATION: 1..21
(D) OTHER INFORMATION: /note= "ETA3: (positive strand)"

-continued

```
    (ix) FEATURE:
          (A) NAME/KEY: misc_feature
          (B) LOCATION: 1..21
          (D) OTHER INFORMATION: /note= "Identified by similarity to
              known sequences and with the assistance of the software
              package "Oligo0" ver. 5.0 for Windows"

(ix) FEATURE:
          (A) NAME/KEY: misc_feature
          (B) LOCATION: 1..21
          (D) OTHER INFORMATION: /note= "Sequence binds to
              complementary sequences within the P. aeruginosa Exotoxin
              A gene and act as primers for PCR-mediated amplification"

(xi) SEQUENCE DESCRIPTION: SEQ ID NO:4:

ACAACGCCCT CAGCATCACC A                                              21

(2) INFORMATION FOR SEQ ID NO:5:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Pseudomonas aeruginosa (ix) FEATURE:
          (A) NAME/KEY: misc_feature
          (B) LOCATION: 1..19
          (D) OTHER INFORMATION: /note= "P. aeruginosa Exotoxin A
              gene, GenBank accession number K01397; NCBI sequence ID
              151215; Found within the published sequence of the
              Exotoxin A gene"

(ix) FEATURE:
          (A) NAME/KEY: primer_bind
          (B) LOCATION: 1..19
          (D) OTHER INFORMATION: /note= "Sequence ends PCR
              amplification only in P. aeruginosa; ETA4:  Negative
              strand"

(ix) FEATURE:
          (A) NAME/KEY: primer_bind
          (B) LOCATION: 1..19
          (D) OTHER INFORMATION: /note= "Sequence binds to
              complementary sequences within the P. aeruginosa Exotoxin
              A gene and act as primers for PCR mediated amplification"

(xi) SEQUENCE DESCRIPTION: SEQ ID NO:5:

CGGGTCGAGC AGGCACAAC                                                 19
```

We claim:

1. A method for detecting the presence of *Pseudomonas aeruginosa* in a fluid sample using a PCR amplification process to amplify a segment of the *P. aeruginosa* exotoxin A gene sequence, said method comprising treating strands of nucleotide fragments with a first and a second oligonucleotide primer that hybridize to a region of said nucleotide fragments wherein said segment has from 400 to about 600 base pairs, wherein said first primer has the sequence 5'-ACA ACG CCC TCA GCA TCA CCA-3' (SEQ ID NO:4) and said second primer has the sequence 5'-CGG GTC GAG CAG GCA CAA C-3' (SEQ ID NO:5), amplifying said segment of the *P. aeruginosa* exotoxin A gene sequence, and detecting said amplified segment, thereby indicating the presence of *P. aeruginosa* in said fluid sample.

2. A method for detecting the presence of *Pseudomonas aeruginosa* in a fluid sample using a PCR amplification process to amplify a segment of the *P. aeruginosa* exotoxin A gene sequence, said method comprising treating strands of nucleotide fragments with a first oligonucleotide primer and a second oligonucleotide primer, each of said oligonucleotide primers having from about 15 nucleotides to about 25 nucleotides, that hybridize to a region of said nucleotide fragments wherein said segment has from 400 to about 600 base pairs, wherein said second oligonucleotide primer has the sequence 5'-CGG GTC GAG CAG GCA CAA C-3' (SEQ ID NO: 5), amplifying said segment of the *P. aerugi-* nosa exotoxin A gene sequence, and detecting said amplified segment, thereby indicating the presence of *P. aeruginosa* in said fluid sample.

3. The method of claim 2 wherein said first oligonucleotide primer has the sequence 5'-ACA ACG CCC TCA GCA TCA CCA-3' (SEQ ID NO:4).

4. A method for detecting the presence of *Pseudomonas aeruginosa* in a fluid sample using a PCR amplification process to amplify a segment of the *P. aeruginosa* exotoxin A gene sequence, said method comprising treating strands of nucleotide fragments with a first and a second oligonucleotide primer, each of said oligonucleotide primers having from about 15 nucleotides to about 25 nucleotides sufficient to hybridize a region of said nucleotide fragments wherein said region has from 400 to about 600 base pairs and said first and second oligonucleotide primers hybridize said nucleotide fragment within the region of 1002 to about 1500 of the *P. aeruginosa* exotoxin A gene wherein said first primer hybridizes to the region 1002 to 1023 of the *P. aeruginosa* exotoxin A gene, and wherein said second primer is complementary to the region 1404 to 1424 of the *P. aeruginosa* exotoxin A gene, and said second oligonucleotide primer has the sequence 5'-CGG GTC GAG CAG GCA CAA C-3' (SEQ ID NO:5), amplifying said segment of the *P. aeruginosa* exotoxin A gene sequence, and detecting said amplified segment, thereby indicating the presence of *P. aeruginosa* in said fluid sample.

5. The method of claim 4 wherein said first oligonucleotide primer has the sequence 5'-ACA ACG CCC TCA GCA TCA CCA-3' (SEQ ID NO:4).

* * * * *